US006265602B1

(12) United States Patent
Voit et al.

(10) Patent No.: US 6,265,602 B1
(45) Date of Patent: Jul. 24, 2001

(54) METHOD FOR HYDROGENATING ALIPHATIC ALPHA-, OMEGA-DINITRILES

(75) Inventors: Guido Voit, Freinsheim; Frank Ohlbach, Dossenheim; Hermann Luyken, Ludwigshafen; Martin Merger, Frankenthal; Alwin Rehfinger, Mutterstadt; Rolf Hartmuth Fischer, Heidelberg; Peter Bassler, Viernheim; Andreas Ansmann, Wiesloch, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/622,800

(22) PCT Filed: Feb. 23, 1999

(86) PCT No.: PCT/EP99/01149

§ 371 Date: Aug. 23, 2000

§ 102(e) Date: Aug. 23, 2000

(87) PCT Pub. No.: WO99/44982

PCT Pub. Date: Sep. 10, 1999

(30) Foreign Application Priority Data

Mar. 6, 1998 (DE) .............................................. 198 09 686

(51) Int. Cl.$^7$ .................................................. C07C 255/00
(52) U.S. Cl. ............................................................ 558/459
(58) Field of Search .............................................. 558/459

(56) References Cited

U.S. PATENT DOCUMENTS

| 5,512,697 | 4/1996 | Schnurr . |
| 5,789,621 | 8/1998 | Schnurr . |
| 5,874,607 | 2/1999 | Schnurr . |

FOREIGN PATENT DOCUMENTS

| 44 46 894 | 7/1996 | (DE) . |
| 19630788 | 9/1997 | (DE) . |
| 19614283 | 10/1997 | (DE) . |
| 93/16034 | 8/1993 | (WO) . |
| 98/43941 | 10/1998 | (WO) . |

*Primary Examiner*—Joseph K. McKane
*Assistant Examiner*—Joseph Murray
(74) *Attorney, Agent, or Firm*—Keil & Weinkauf

(57) ABSTRACT

A process for hydrogenation of aliphatic alpha, omega-dinitriles in the presence of a heterogeneous fixed bed catalyst comprises using a reaction mixture comprising from 2 μmol to 30 mmol NA, K, Rb, Cs, Mg, Ca, Sr, Ba or Mn or mixtures thereof in the form of a basic salt, based on 10 mol of aliphatic alpha, omega-dinitrile used.

9 Claims, No Drawings

METHOD FOR HYDROGENATING ALIPHATIC ALPHA-, OMEGA-DINITRILES

This application is a 371 of PCT/EP99/01149 filed Feb. 23, 1999.

The present invention relates to a process for hydrogenation of aliphatic alpha, omega-dinitriles in the presence of a heterogeneous fixed bed catalyst, which comprises using a reaction mixture comprising from 2 μmol to 30 mmol Na, K, Rb, Cs, Mg, Ca, Sr, Ba or Mn or mixtures thereof in the form of a basic salt, based on 10 mol of aliphatic alpha, omega-dinitrile used.

Processes for preparing aliphatic alpha, omega-aminonitriles or alpha, omega-diamines by hydrogenation of aliphatic alpha, omega-dinitriles in the presence of a heterogeneous fixed bed catalyst are common knowledge.

A disadvantage with these processes is the formation of major amounts of undesirable by-products. For instance, the hydrogenation of adiponitrile (ADN) to form a mixture of 6-aminocapronitrile (ACN) and hexamethylenediamine (HMD) byproduces especially tetrahydrazepine (THA) of the formula (I)

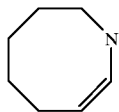

I which is difficult to separate from the product or product mixture, in amounts of more than 1000 ppm (based on HMD).

DE-A 44 46 894 discloses hydrogenating ADN to a mixture of ACN and HMD over an Ni, Ru, Rh or Co catalyst, in the suspension mode especially, by adding lithium hydroxide to the reaction mixture to increase the ACN yield.

WO-A 93/16034 discloses hydrogenating ADN to a mixture of ACN and HMD over a Raney Ni catalyst in the suspension mode by adding lithium hydroxide, sodium hydroxide or potassium hydroxide to the reaction mixture to increase the ACN yield.

Unfortunately, the suspension process over Raney catalysts raises the THA level to more than 1% by weight (based on HMD).

It is an object of the present invention to provide a process for the hydrogenation of aliphatic alpha, omega-dinitriles in the presence of a heterogeneous fixed bed catalyst without the aforementioned disadvantages and with the capability of enabling the production of aliphatic alpha, omega-aminonitriles and/or alpha, omega-diamines to take place in a technically simple and economical manner.

We have found that this object is achieved by the process defined at the beginning.

The starting materials used in the process of the present invention are aliphatic alpha,omega-dinitriles of the general formula II $NC—(CH_2)_n—CN$     II where n is an integer from 1 to 10, especially 2, 3, 4, 5 or 6. Particularly preferred compounds I are succinonitrile, glutaronitrile, adiponitrile, pimelonitrile and suberonitrile, most preferably adiponitrile.

The process of the present invention partially hydrogenates the above-described dinitriles II, preferably in the presence of a solvent, using a heterogeneous fixed bed catalyst to form alpha,omega-aminonitriles of the general formula III $NC—(CH_2)_n—CH_2—NH_2$     III and/or alpha, omega-diamines of the general formula IV $H_2N—CH_2—(CH_2)n—CH_2—NH_2$ IV, where n is as defined above. Particularly preferred aminonitriles III are those where n is 2, 3, 4, 5 or 6, especially 4, i.e., 4-aminobutanenitrile, 5-aminopentanenitrile, 6-aminohexanenitrile ("6-aminocapronitrile"), 7-aminoheptanenitrile and 8-aminooctanenitrile, most preferably 6-aminocapronitrile.

Particularly preferred diamines IV are those where n is 2, 3, 4, 5 or 6, especially 4, i.e. 1,4-diaminobutane, 1,5-diaminopentane, 1,6-diaminohexane (HMD), 1,7-diaminoheptane and 1,8-diaminooctane, most preferably HMD.

Similarly, the coproduction of ACN and HMD is most preferable.

The partial hydrogenation can preferably be carried out batchwise or continuously in a fixed bed reactor in trickle or upflow mode, in which case it is customary to select a temperature within the range from 20 to 150° C., preferably within the range from 30 to 120° C., and a pressure which is generally within the range from 2 to 40 MPa, preferably within the range from 3 to 30 MPa. The partial hydrogenation can advantageously be carried out in the presence of a solvent, preferably ammonia, amines, diamines and triamines having from 1 to 6 carbon atoms such as trimethylamine, triethylamine, tripropylamine and tributylamine or alcohol, preferably methanol and ethanol, particularly preferably ammonia. In a preferred embodiment, ammonia is chosen within the range from 0.5 to 10, preferably from 0.5 to 6, g per g of adiponitrile. The catalyst space velocity chosen is preferably within the range from 0.1 to 2.0, preferably within the range from 0.3 to 1.0, kg of adiponitrile/L*h. Here, too, the residence time can be varied to control the conversion and hence the selectivity in a specific manner.

In the case of aolipoolinitrile [sic] as dinitrile, the molar ratio of 6-aminocapronitrile to hexamethylenediamine, and hence the molar ratio of caprolactam to hexamethylenediamine, can be controlled by means of the particular choice of adiponitrile conversion. Preference is given to using adiponitrile conversions within the range from 10 to 90%, preferably within the range from 30 to 80%, to obtain high 6-aminocapronitrile selectivity.

In general, the sum of 6-aminocapronitrile and hexamethylenediamine is within the range from 98 to 99%, depending on catalyst and reaction conditions.

According to the invention, the hydrogenation is carried out in such a way that the reaction mixture comprises from 2 μmol to 30 mmol, preferably from 10 μmol to 3 mmol, especially from 10 μmol to 300 μmol, of Na, K, Rb, Cs, Mg, Ca, Sr, Ba or Mn or mixtures thereof, preferably Na, K or Ca or mixtures thereof, especially Ca, in the form of a basic organic, preferably inorganic, salt (V), such as carbonate, preferably oxide, especially hydroxide, or mixtures thereof, based on 10 mol of aliphatic alpha, omega-dinitrile used.

Particular preference is given to such a salt (V) which is fully soluble in the reaction mixture.

A salt (V) can be added to the reaction mixture prior to the hydrogenation dissolved, preferably, in at least one of the constituents of the reaction mixture or in solid form. It is also possible to add a salt (V) to the reaction mixture during the hydrogenation, in which case the advantageous effect is less compared with an addition prior to the hydrogenation.

The hydrogenation can be carried out in princple according to one of the known processes by, in general, conducting the hydrogenation in the presence of nickel, cobalt, iron or rhodium catalysts. These catalysts can be used as supported catalysts or as unsupported catalysts. Examples of possible catalyst supports are aluminum oxide, silicon dioxide, titanium dioxide, magnesium oxide, activated carbons and spinels.

In a preferred embodiment, the dinitrile is hydrogenated at elevated temperature and elevated pressure in the presence of a solvent and of a heterogeneous fixed bed catalyst by using a catalyst containing (a) a compound based on a metal selected from the group consisting of nickel, cobalt, iron, ruthenium and rhodium, and (b) from 0.01 to 25%, preferably from 0.1 to 5%, by weight, based on (a), of a promoter based on a metal selected from the group consisting of palladium, platinum, iridium, osmium, copper, silver, gold, chromium, molybdenum, tungsten, manganese, rhenium, zinc, cadmium, lead, aluminum, tin, phosphorus, arsenic, antimony, bismuth and rare earth metals, and also (c) from 0 to 5%, preferably from 0.1 to 3%, by weight, based on (a), of a compound based on an alkali metal or on an alkaline earth metal, with the proviso that, if a compound based on only ruthenium or rhodium or ruthenium and rhodium or nickel and rhodium is chosen as component (a), the promoter (b) can be dispensed with, if desired, and also with the further proviso that component (a) is not based on iron when component (b) is aluminum.

Preferred catalysts are those in which component (a) contains at least one compound based on a metal selected from the group consisting of nickel, cobalt and iron in an amount within the range from 10 to 95% by weight and also ruthenium and/or rhodium in an amount within the range from 0.1 to 5% by weight, each percentage being based on the sum total of components (a) to (c), component (b) contains at least one promoter based on a metal selected from the group consisting of silver, copper, manganese, rhenium, lead and phosphorus in an amount within the range from 0.1 to 5% by weight, based on (a) and component (c) contains at least one compound based on the alkali metals and alkaline earth metals selected from the group consisting of lithium, sodium, potassium, cesium, magnesium and calcium, in an amount within the range from 0.1 to 5% by weight.

Particularly preferred catalysts are:

catalyst A containing 90% by weight of cobalt oxide (CoO), 5% by weight of manganese oxide ($Mn_2O_3$), 3% by weight of phosphorus pentoxide and 2% by weight of sodium oxide ($Na_2O$), catalyst B containing 20% by weight of cobalt oxide (CoO), 5% by weight of manganese oxide ($Mn_2O_3$), 0.3% by weight of silver oxide ($Ag_2O$), 70% by weight of silicium dioxide ($SiO_2$), 3.5% by weight of aluminum oxide ($Al_2O_3$), 0.4% by weight of iron oxide ($Fe_2O_3$), 0.4% by weight of magnesium oxide (MgO) and also 0.4% by weight of calcium oxide (CaO), and catalyst C containing 20% by weight of nickel oxide (NiO), 67.42% by weight of silicon dioxide ($SiO_2$), 3.7% by weight of aluminum oxide ($Al_2O_3$), 0.8% by weight of iron oxide ($Fe_2O_3$), 0.76% by weight of magnesium oxide (MgO), 1.92% by weight of calcium oxide (CaO), 3.4% by weight of sodium oxide ($Na_2O$) and also 2.0% by weight of potassium oxide ($K_2O$).

In a further preferred embodiment, the dinitrile is hydrogenated at elevated temperature and elevated pressure in the presence of a solvent and of a heterogeneous fixed bed catalyst (a) metallic cobalt, a cobalt compound or mixtures thereof, the proportion of metallic cobalt based on (a) being within the range from 20 to 100% by weight, (b) from 10 to 70% by weight based on (a) of metallic iron, iron oxide, a further iron compound or mixtures thereof, the proportion of iron oxide based on (b) being within the range from 20 to 100% by weight, (c) from 0 to 1% by weight based on the sum total of (a) and (b) of a compound based on alkali metal, alkaline earth metal or zinc.

Preference is given to those catalysts whose proportion in the catalyst precursor prior to activation with hydrogen or a gas mixture comprising hydrogen and an inert gas such as nitrogen over one or more Co compounds, calculated as cobalt(II) oxide, is within the range from 10 to 80% by weight, preferably within the range from 20 to 70% by weight, especially within the range from 30 to 60% by weight.

Preference is given to those catalysts whose proportion in the catalyst precursor prior to activation with hydrogen or a gas mixture comprising hydrogen and an inert gas such as nitrogen over one or more Fe compounds, calculated as iron(III) oxide, is within the range from 20 to 90% by weight, preferably within the range from 30 to 60% by weight, especially within the range from 40 to 70% by weight.

These catalysts can be supported or unsupported catalysts. Examples of possible support materials are porous oxides such as aluminum oxide, silicon dioxide, alumosilicates, lanthanum oxide, titanium dioxide, zirconium dioxide, magnesium oxide, zinc oxide and zeolites and also activated carbon or mixtures thereof.

Preparation is generally by precipitating one or more precursors of component (a) together with precursors of component (b) and, if desired, with one or more precursors of trace component (c) in the presence or absence of support materials (depending on which catalyst type is desired), if desired processing the resulting catalyst precursor into extrudates or tablets, drying and then calcining. Supported catalysts are generally also obtainable by saturating the support with a solution of (a), (b) and if desired (c), it being possible to add the individual components simultaneously or in succession, or by spraying the components (a), (b) and if desired (c) onto the support in a conventional manner.

Suitable precursors for components (a) and (b) are generally readily water-soluble salts of the aforementioned metals such as nitrates, chlorides, acetates, formates and sulfates, preferably nitrates.

Suitable precursors for component (c) are generally readily water-soluble salts of alkali metals or alkaline earth metals such as lithium, sodium, potassium, rubidium, cesium, magnesium or calcium, or zinc and also mixtures thereof, such as hydroxides, carbonates, nitrates, chlorides, acetates, formates and sulfates, preferably carbonates and hydroxides.

Precipitation is generally effected from aqueous solutions, alternatively by adding precipitating reagents, by changing the pH or by changing the temperature.

Precipitating reagents used can be for example ammonium carbonate or hydroxides or carbonates of the alkali metals. If alkali metal compound reagents are used, it is advisable to free the precipitates from adhering alkali metal compounds, for example by washing off with water. This can be carried out directly after removal of the precipitate from the mother liquor or after a drying and calcining step. Drying can be carried out in a conventional manner, preferably in spray towers, in which case the precipitate is generally slurried up in a liquid, advantageously water. The catalyst material thus obtained is customarily dried at temperatures which are generally within the range from 80 to 150° C., preferably within the range from 80 to 120° C.

Calcining is customarily effected at temperatures within the range from 150 to 500° C., although in individual cases temperatures of up to 1000° C. can be suitable, preferably within the range from 200 to 450° C. in a gas stream comprising air or nitrogen in suitable apparatus for this purpose such as tray or rotary tube ovens.

The powder can be processed in a conventional manner into shaped articles, such as extrudates or tablets, especially if the catalyst material is to be used in a fixed bed.

In the preparation of extrudates, assistants such as inorganic acids, organic acids or bases such as ammonia can be added, and the assistants can contain cobalt or iron compounds. After extrusion, the extrudates can be dried at temperatures below 200° C. and calcined at temperatures within the range from 150 to 500° C., although in individual cases temperatures of up to 1000° C. can be suitable, preferably within the range from 200 to 450° C. in a gas stream comprising air or nitrogen in suitable apparatus for this purpose such as tray or rotary tube ovens.

In the preparation of tablets, organic or inorganic assistants such as stearates, graphite or talc can be added.

After calcining, the catalyst material is subjected to a reducing atmosphere ("activation"), for example by subjecting it to a temperature within the range from 150 to 300° C., preferably within the range from 200 to 280° C., to a hydrogen atmosphere or a gas mixture comprising hydrogen and an inert gas such as nitrogen for a period within the range from 2 to 96 hours. The volume hourly space velocity for this is within the range from 200 to 2000 L per L of catalyst per hour.

Advantageously, the activation of the catalyst is carried out directly in the synthesis reactor, since this customarily obviates an otherwise necessary intermediary step, namely the passivation of the surface by means of oxygen-nitrogen mixtures such as air at customarily temperatures within the range from 20 to 80° C., preferably within the range from 25 to 35° C. The activation of passivated catalysts is then preferably carried out in the synthesis reactor in a hydrogen-comprising atmosphere at a temperature within the range of 150 to 300° C., preferably within the range from 200 to 280° C.

The catalysts contain
(a) metallic cobalt, a cobalt compound or mixtures thereof, the proportion of metallic cobalt, based on (a), being within the range from 20 to 100% by weight, preferably within the range from 30 to 90% by weight, especially within the range from 40 to 70% by weight,
(b) from 10 to 70% by weight, based on (a), of metallic iron, iron oxide, a further iron compound or mixtures thereof, the proportion of iron oxide based on (b) being within the range from 20 to 100% by weight, preferably within the range from 20 to 80% by weight, especially within the range from 30 to 70% by weight, and
(c) from 0 to 1% by weight, based on the sum total of (a) and (b), of a compound based on alkali metal, alkaline earth metal or zinc.

The catalysts can be used as fixed bed catalysts in upflow or trickle mode.

Particularly preferred catalysts are those which contain
a) a compound based on iron such as iron oxide and
b) from 0 to 5% by weight based on (a) of a promoter based on an element or 2,3,4 or 5 elements selected from the group consisting of aluminum, silicon, zirconium, vanadium and titanium, and also
c) from 0 to 5% by weight, preferably from 0.1 to 3% by weight, especially from 0.1 to 0.5% by weight, based on (a), of a compound based on an alkaline or alkaline earth metal, preferably selected from the group consisting of lithium, sodium, potassium, rubidium, cesium, magnesium and calcium.

These catalysts can be supported or unsupported catalysts. Examples of possible support materials are porous oxides such as aluminum oxide, silicon dioxide, alumosilicates, lanthanum oxide, titanium dioxide, zirconium dioxide, magnesium oxide, zinc oxide and zeolites and also activated carbon or mixtures thereof.

Preparation is generally by precipitating precursors of components (a) together with precursors of the promoters (components (b)) and, if desired, with precursors of trace components (c) in the presence or absence of support materials (depending on which catalyst type is desired), if desired processing the resulting catalyst precursor into extrudates or tablets, drying and then calcining. Supported catalysts are generally also obtainable by saturating the support with a solution of (a), (b) and if desired (c), it being possible to add the individual components simultaneously or in succession, or by spraying the components (a), (b) and if desired (c) onto the support in a conventional manner.

Suitable precursors for components (a) are generally readily water-soluble salts of the aforementioned metals such as nitrates, chlorides, acetates, formates and sulfates, preferably nitrates.

Suitable precursors for components (b) are generally readily water-soluble salts or complex salts of the aforementioned metals such as nitrates, chlorides, acetates, formates and sulfates and also in particular hexachloroplatinate, preferably nitrates and hexachloroplatinate.

Suitable precursors for components (c) are generally readily water-soluble salts of the aforementioned alkali metals and alkaline earth metals such as hydroxides, carbonates, nitrates, chlorides, acetates, formates and sulfates, preferably hydroxides and carbonates.

Precipitation is generally effected from aqueous solutions, alternatively by adding precipitating reagents, by changing the pH or by changing the temperature.

The catalyst prematerial thus obtained is customarily dried at temperatures which are generally within the range from 80 to 150° C., preferably within the range from 80 to 120° C.

Calcining is customarily effected at temperatures within the range from 150 to 500° C., preferably within the range from 200 to 450° C. in a gas stream comprising air or nitrogen.

The powder can be processed in a conventional manner into shaped articles, such as extrudates or tablets, especially if the catalyst material is to be used in a fixed bed.

After calcining, the catalyst material obtained is generally subjected to a reducing atmosphere ("activation"), for example by subjecting it to a temperature within the range from 80 to 250° C., preferably within the range from 80 to 180° C., in the case of catalysts based on ruthenium or rhodium as component (a) or to within the range from 200 to 500° C., preferably from 250 to 400° C., in the case of catalysts based on one of the metals selected from the group consisting of nickel, cobalt and iron as component (a) to a hydrogen atmosphere or a gas mixture comprising hydrogen and an inert gas such as nitrogen for a period within the range from 2 to 24 h. The volume hourly space velocity for this is preferably 200 L per L of catalyst per hour.

Advantageously, the activation of the catalyst is carried out directly in the synthesis reactor, since this customarily obviates an otherwise necessary intermediary step, namely the passivation of the surface by means of oxygen-nitrogen mixtures such as air at customarily temperatures within the range from 20 to 80° C., preferably within the range from 25 to 35° C. The activation of passivated catalysts is then preferably carried out in the synthesis reactor in a hydrogen-comprising atmosphere at a temperature within the range of 180 to 500° C., preferably within the range from 200 to 350° C.

The catalysts can be used as fixed bed catalysts in upflow or trickle mode.

The process of the present invention provides alpha, omega-aminonitriles and/or alpha, omega-diamines in good selectivities and with only minor quantities of unwanted by-products. alpha,omega-Aminonitriles and alpha, omega-diamines are important starting compounds for preparing cyclic lactams, especially 6-aminocapronitrile for caprolactam and HMD.

EXAMPLES a) Catalyst Preparation

The catalysts were prepared by heating a magnetite ore under nitrogen at 1500° C. for 6 hours. The magnetite ore used had the following composition:

72% by weight of Fe
0.07% by weight of Al
0.03% by weight of Ca
0.04% by weight of Mg
0.11% by weight of Si
0.01% by weight of Ti
remainder oxygen The cooled melt block was comminuted in a jaw crusher, and a sieve fraction of particle size 3–6 mm was separated out by sieving. The oxidic catalyst was reduced in a hydrogen/nitrogen stream at 450° C. for 72 h and then passivated in a nitrogen/air stream (24 h with 1% by volume of air in nitrogen) at below 45° C.

b) Hydrogenation

Comparative Example

A tubular reactor (180 cm in length, 30 mm in diameter) was packed with 740 mL (1816 g) of the catalyst material prepared according to (a) and reduced in a hydrogen stream (500 standard L/h) at 150 bar. In the process, the temperature was raised from 30° C. to 340° C. over 24 h and then maintained at 340° C. for 72 h.

After the temperature had been lowered, the reactor was fed with a mixture of 400 mL/h of ADN, 770 g/h of ammonia and 500 standard L/h of hydrogen at 250 bar. At 100° C., the ADN conversion was 70%, the ACN selectivity was 60%, and the total selectivity for ACN and HMD was 99%.

The THA content in the hydrogenation effluent was 1200 ppm, based on HMD.

Inventive Example 1

The comparative example was repeated except that the ADN had added to it 9.62 µmol of CaO based on 10 mol of ADN.

The THA content in the hydrogenation effluent was 400 ppm, based on HMD.

Inventive Example 2

The comparative example was repeated except that the ADN had added to it 72.9 µmol of $Ca(OH)_2$ based on 10 mol of ADN.

The THA content in the hydrogenation effluent was 300 ppm, based on HMD.

We claim:

1. A process for hydrogenation of aliphatic alpha, omega-dinitriles in the presence of a heterogeneous fixed bed catalyst, which comprises using a reaction mixture comprising from 2 µmol to 30 mmol Ca in the form of a basic salt, based on 10 mol of aliphatic alpha, omega-dinitrile used.

2. A process as claimed in claim 1, wherein the heterogeneous catalyst used comprises an active component based on iron, cobalt, nickel, rhodium or ruthenium or their compounds or their mixtures.

3. A process as claimed in claim 1, wherein the heterogeneous catalyst used comprises an active component based on iron.

4. A process as claimed in claim 1, wherein the catalyst is a supported catalyst.

5. A process as claimed in claim 1, wherein the catalyst is an unsupported catalyst.

6. A process as claimed in claim 1, wherein the dinitrile used is adiponitrile to obtain 6-aminocapronitrile.

7. A process as claimed in claim 1, wherein the dinitrile used is adiponitrile to obtain hexamethylene-diamine.

8. A process as claimed in claim 1 wherein the aliphatic alpha, omega dinitrile is adiponitrile, and a mixture of 6-aminocapronitrile and hexamethylenediamine is produced.

9. A process as claimed in claim 7, further comprising the steps of
(1) partial hydrogenation of adiponitrile to obtain a mixture comprising 6-aminocapronitrile, hexamethylene-diamine and adipodinitrile and
(2) removing 6-aminocapronitrile and hexamethylenediamine from the mixture.

* * * * *